United States Patent [19]

Narayanan et al.

[11] Patent Number: 5,419,761

[45] Date of Patent: May 30, 1995

[54] LIPOSUCTION APPARATUS AND ASSOCIATED METHOD

[75] Inventors: Krishna Narayanan; Marc Liang, both of Pittsburgh, Pa.; Howard M. Alliger, Melville, N.Y.

[73] Assignee: Misonix, Inc., Farmingdale, N.Y.

[21] Appl. No.: 101,188

[22] Filed: Aug. 3, 1993

[51] Int. Cl.$^6$ ............................................. A61B 17/20
[52] U.S. Cl. ................................................ 604/22
[58] Field of Search ........................... 604/22; 128/24; 606/169, 171

[56] References Cited

U.S. PATENT DOCUMENTS

| | | | |
|---|---|---|---|
| 4,040,414 | 8/1977 | Suroff . | |
| 4,136,700 | 1/1979 | Broadwin et al. . | |
| 4,223,676 | 9/1980 | Wuchinich et al. . | |
| 4,634,419 | 6/1987 | Kreizman et al. | 604/22 |
| 4,735,605 | 4/1988 | Swartz . | |
| 4,886,491 | 12/1989 | Parisi et al. . | |
| 4,920,954 | 5/1990 | Alliger et al. . | |
| 4,922,902 | 5/1990 | Wuchinich et al. . | |
| 4,989,588 | 2/1991 | Kubota et al. | 604/22 |
| 5,026,387 | 6/1991 | Thomas | 604/22 |
| 5,069,664 | 12/1991 | Guess et al. . | |
| 5,112,300 | 5/1992 | Ureche | 604/22 |
| 5,123,903 | 6/1992 | Quaid et al. . | |
| 5,151,084 | 9/1992 | Khek | 604/22 |
| 5,151,085 | 9/1992 | Sokuvsi et al. | 604/22 |
| 5,209,719 | 5/1993 | Baruch et al. | 604/22 |
| 5,222,937 | 6/1993 | Kagowa | 604/22 |
| 5,263,957 | 11/1993 | Davidson | 604/22 |
| 5,279,547 | 1/1994 | Costin | 604/22 |
| 5,282,820 | 2/1994 | Goodstein | 604/22 |

*Primary Examiner*—C. Fred Rosenbaum
*Assistant Examiner*—Manuel Mendez
*Attorney, Agent, or Firm*—R. Neil Sudol; Henry Coleman

[57] ABSTRACT

A method for removing adipose tissue uses an elongate rigid tube or probe member having a distal end and a proximal end and an axially extending lumen. An incision is formed in a skin surface of a patient, the tube being inserted through the incision into subcutaneous adipose tissues of the patient. Upon insertion of the tube through the incision, an ultrasonic pressure wave is generated at the proximal end of the tube, the waveform being transmitted through the tube to establish a standing wave therein. The standing ultrasonic wave in the insertion tube produces cavitation bubbles at the distal end of the tube, the bubbles causing liquefaction of adipose tissues of the patient at a surgical site located distally of the distal end of the insertion tube. Suction is applied to the lumen of the tube, thereby aspirating the liquefied adipose tissues from the surgical site through the lumen. During the entire procedure, the distal end of the tube and the adipose tissues at the surgical site are maintained at approximately body temperature.

29 Claims, 2 Drawing Sheets

LIPOSUCTION APPARATUS AND ASSOCIATED METHOD

BACKGROUND OF THE INVENTION

This invention relates to a liposuction apparatus and method. More particularly, this invention relates to a liposuction apparatus having an ultrasonic handpiece with an axial suction passage, and is ideally suited for smooth continuous fat removal.

Liposuction, which literally means "fat suction", is a technique that pulls fat out of the body by means of scraping and suction. It can be used to reduce the volume of fat in almost all regions of the body, but is particularly effective in areas such as thighs and abdomen, which contain genetically determined fat not responsive to diet or exercise. Liposuction is currently an established modality in cosmetic surgery, performed by surgeons as an elective operation, and is one of the fastest-growing procedures in medicine.

All existing liposuction devices used in surgery however, cause complications and trauma.

The first reported fat removal procedure was performed in Europe in 1929. Since that time, surgeons have tried common instruments such as surgical knives, scalpels and curettes to remove excess body fat. Also tried were uncommon instruments such as a motorized cutting blade devised by the Fischers, a father-and-son team and early innovators in Italy in or about 1975. Through the years, tools have changed considerably, from sharp knives to blunt cannulas, but fat removal procedures (old or new) are still considered risky and produce inconsistent results. Complications arise mostly due to damaged blood vessels. As a result, organized semi-solid blood clots known as "hematoma" form causing damage to overlying skin and contour irregularities. Other complications, such as seroma formation (the collection of body fluids) can produce infecton and wrinkles. Nerve conduction is also usually affected. Further, too much fat is sometimes removed form the wrong place, resulting in misshaping of the remaining tissue. Lastly, liposuction procedures are time consuming and tedious for both the surgeon and the patient.

The most commonly accepted liposuction technique utilizes a cannula with a blunt closed tip rather than an open tip or a pointed or sharpened tip. This cannula is a metal tube, about the size of a pencil, which is attached to a suction pump. The cannula, with its rounded tip, is sometimes passed through the fat first, without suction, to develop the proper passageways. Then suction is applied and the surgeon continues passing the cannula through the fat tunnels with repeated radial thrusts and on several levels of the tissue. Adipose tissue is aspirated through a hole in the side of the cannula near its distal end. The cannula must be moved back and forth about ten times through each tunnel. Problems associated with this technique are similar to those experienced with the older methods of liposuction. Even with a blunt edge at the distal end of the cannula, fat globules are torn off by both scraping and suction power at the side hole. The bleeding is also similar in amount to that resulting from the use of the older, sharp-edged instruments which cut fat tissue and blood vessels without suction.

The first few minutes of treatment with the blunt cannula technique will usually yield 90% fat and 10% blood. As the treatment continues, an increase in blood content is observed which soon measures 90% blood and 10% tissue. Studies reveal an average of approximately 30% blood in the trap bottle at the end of the procedure. Trauma to the blood vessels ultimately reduces circulation to overlying skin and may cause skin necrosis. Almost all patients have swelling and are often dramatically black and blue for 3–6 weeks. Approximately half will notice some hypesthesia or loss of feeling in the treated area for two to three months. All patients need about six months for improvement to be complete.

Besides causing excess bleeding, current liposuction techniques are also somewhat clumsy in that the surgeon has little sensitivity as to how much fat is being removed during scraping and suction. Consequently, this surgery almost always results in the removal of too much adipose tissue or too little. In addition, a certain amount of fat destroyed by the mechanical action of the cannula is not aspirated. This remaining material can lead to dimpling and other defects. Liposuction that is too aggressive, although achieving a pleasing contour at the end of the procedure, may result in defects that are difficult or impossible to correct. Nevertheless, despite the many risks and drawbacks, thousands of liposuction procedures are performed using the blunt cannula technique.

Fat removal and liposuction has had a checkered history, and for many years was not an accepted modality in the United States. The first reported fat removal through a small incision was by a French surgeon in or about 1929, and resulted in major injuries to blood vessels. Later, a leg had to be amputated. Major developments in liposuction occurred in the late 1970's, and what began as an exploratory technique performed with instruments designed for other purposes became an established modality with novel surgical instrumentation of its own. Interestingly enough, however, none of the present instruments have been accepted by the U.S. Food and Drug Administration.

Although liposuction was developed mainly in Europe, two Americans were early innovators. Wilkerson, practicing in Hawaii in 1968, had acceptable results but abandoned the method because of inadequate instrumentation. Teimourian, working in Bethesda, Maryland in 1976, came upon suction aspiration by accident, and then continued with his new operation with a suction assisted curette. Liposuction was finally popularized by Illouz of France who developed the blunt cannula and the "bicycle spoke" method of removal. He also coined the term "lypolysis."

In 1983, The American Society of Plastic and Reconstructive Surgeons, after evaluating the Illouz procedure in Paris by a blue ribbon committee, "unanimously agreed that suction lipectomy by the Illouz blunt cannula method is a surgical procedure that is effective in trained and experienced hands and offers benefits which heretofore have been available." Currently over 120,000 liposuction operations are performed annually by plastic surgeons in the U.S., and almost an equal number by gynecologists, general surgeons, and ear, nose and throat surgeons. There is also a lipoplasty magazine published by the Lipoplasty Society of North America.

Today there exists a wide variety of cannulas which allow surgeons to work more skillfully. For example, there is a more aerodynamic, bullet shaped tip, or curette-cannula where the suction hole has a sharp edge, or a cannula with a star shaped tip to better loosen the fat, and a spatula-extractor for removing hematoma. Nevertheless, it is still difficult to consistently avoid discoloration, contour irregularities, and cellulite formation which occur as complications ("Liposuctions' Popularity spells Risks," by David Holthaus, Hospitals, February 1988). And as pointed out by Sy Montgomery in "Vacuuming the Fat Away," Working Woman, May 1988, "while it's usually true that after liposuction you'll probably look better in clothes, you might look worse in a bathing suit."

Two of the very earliest uses of "destructive" ultrasound on the body were reported in "Physical Factors Involved in Ultrasonically Induced Changes in Living Systems, Identification of Non-Thermal Effects," by Fry W. J., Acoust, Soc Am 22(6):867,1950; and "An Ultrasonic Unit for the Treatment of Menier's Disease," by Johnson, S. J., Ultrasonics, 5, 173–176, 1967. The latter article described the curing of a middle ear disease earlier, in 1958. The now familiar ultrasonic probes for body tissue removal were developed around 1970 (see U.S. Pat. No. 3,589,363 to Banko and U.S. Pat. No. 3,526,219 to Balamuth) and have been in commercial use for about 15 years. There are perhaps 100 patents describing such ultrasonic devices; U.S. Pat. No. 4,750,902 to Wuchinich lists 40. Nevertheless, at present, there is no commercial use of ultrasound for fat removal liposuction. This is especially surprising since liposuction has been one of the fastest growing medical procedures. A better operative method here would prove both practical and lucrative, as well as probably expand the field. An abdominal liposuction procedure, for example, costs $3,000 to $6,000; a facial procedure on chin and neck, about $2,000, and breast reduction about $2,000. Surprisingly, too, there are no papers in the scientific literature using ultrasonic probes for fat removal, though there are published papers describing the use of ultrasonic probes on almost every other type of tissue, including the liver, pancreas, kidney, testes, stomach, mucosa, cataracts, spinal cord, brain, nerves, rectum, spleen, lung, gastrointestinal tract, arteries, faeces, plasma, collagen, retina and kidney stones. There seems to be a clear need for a new or specialized instrument.

Although an ultrasonic probe for liposuction was granted in 1989 to Parisi, U.S. Pat. No. 4,886,491, there is no evidence that the probe has ever been actually reduced to practice or put into commercial use at least in the United States, despite the great need for an improved liposuction procedure. In accordance with the disclosure of Parisi, fat is melted by localized frictional heat produced by the vibrating probe. Heat however, is dangerous in that it may adversely affect other tissues such as muscle or nerve.

The ultrasonic probe of Parisi is provided at the distal end with a large lateral hole, similar to standard liposuction cannulas. This hole would make his cannula difficult to tune, as well as increase the impedance and require extra power. There is also the risk of cannula breakage, since the hole or holes in the Parisi probes occupy a large percentage of the circumference. The hole or holes are also near a node (point of no movement) where stress is maximum. In order to achieve a 2 mil amplitude at 40 kHz, Parisi's probe as pictured would likely heat an inordinate amount along the length. In addition, the hole or holes at the side of Parisi's probe will scrape tissue and blood vessels similar to the older methods.

Parisi's patent does not address the important question of hematoma or seroma removal. These formations apparently cannot be melted or separated by the method of Parisi.

A prior art tissue removal apparatus and associated method are described in U.S. Pat. No. 4,886,491 issued December 1989. Related patents include U.S. Pat. Nos. 4,223,676, 3,589,363 to Banko, U.S. Pat. No. 3,526,219 to Balamuth, U.S. Pat. No. 4,861,331 to Parisi, and U.S. Pat. No. 4,750,902. Another related patent, which is assigned to one of the same assignees as the present invention is U.S. Pat. No. 4,902,954.

Lastly, in using the probe of Parisi, it would be necessary to move the probe in and out, as well as twist it, in order to collect the separated, melted and emulsified fat.

OBJECTS OF THE INVENTION

An object of the present invention is to provide an improved method for the removal of adipose tissues.

Another object of the present invention is to provide such a method which minimizes injury to nerves and blood vessels and which minimizes overall trauma to tissues during a liposuction procedure.

Another, related, object of the present invention is to provide such a method wherein blood loss is minimized.

A further object of the present invention is to provide a liposuction method which yields a more even reshaping of overlying skin surfaces than conventional procedures.

A more particular object of the present invention is to provide such a method wherein the diameter of tunnels or channels formed in adipose tissue is minimized.

An associated particular object of the present invention is to provide such a method wherein the size of the skin incision is minimized.

A further particular object of the present invention is to provide such a method wherein the tunnels in the adipose tissue are smooth and wherein the gouging which occurs with liposuction probes having water jackets or sleeves is avoided.

Yet another particular object of the present invention is to provide a liposuction method wherein the surgeon knows where and how much fat is being removed.

An associated object of the present invention is to provide such a method which allows a liposuction probe to be accurately positioned and tissue removal to be spot specific.

Additional objects of the present invention include the provision of an ultrasonic liposuction probe which minimizes injury to nerves and blood vessels and which minimizes overall trauma to tissues during a liposuction procedure, which reduces blood loss relative to other liposuction procedures, which yields a more even reshaping of overlying skin surfaces than conventional procedures, and/or which enables a surgeon to know where and how much fat is being removed.

These and other objects of the present invention will be apparent from the drawings and detailed descriptions herein.

SUMMARY OF THE INVENTION

A method for removing adipose tissue comprises, in accordance with the present invention, the steps of (a) providing an elongate rigid tube or probe member having a distal end and a proximal end and an axially extending lumen, (b) forming an incision in a skin surface of a patient, (c) inserting only the tube (without a surrounding water jacket) through the incision into subcutaneous adipose tissues of the patient, (d) upon insertion of the tube through the incision, generating an ultrasonic pressure wave at the proximal end of the tube, (e) transmitting the ultrasonic wave through the tube to establish a standing wave therein, (f) producing cavitation bubbles at the distal end of the tube in response to the ultrasonic standing wave, (g) liquefying adipose tissues of the patient, by virtue of the production of the cavitation bubbles, at a surgical site located distally of the distal end of the insertion tube, (h) applying suction to the lumen of the tube, thereby aspirating the liquefied adipose tissues from the surgical site through the lumen, and (i) maintaining the distal end of the tube and the adipose tissues at the surgical site at approximately body temperature during the production of cavitation bubbles and the liquefaction of the fatty tissues.

According to another feature of the present invention, the method further comprises the step of delivering a surgical liquid to the surgical site during the production of cavitation bubbles and the liquefaction of the fatty tissues. This additional step includes the step of guiding the liquid in a film along an external surface of the tube towards the distal end thereof. More particularly, in accordance with a specific embodiment incorporating this feature of the invention, the liquid may be maintained in the film on the external surface of the tube solely by adhesion of the liquid to the external surface of the tube. There is no ancillary tube or guide extending coaxially with the tube or parallel thereto. Accordingly, only the insertion tube or ultrasonic probe member is inserted through the incision into the subutaneous fatty tissues.

In an alternative specific embodiment of the invention, the tube is provided along the external surface with at least one longitudinally extending groove, the liquid being transferred at least partially along the groove toward the distal end.

Where the distal end of the insertion tube or probe undergoes a reciprocating motion due to the standing wave, the method advantageously further comprises the steps of monitoring amplitude of the reciprocating motion and monitoring power consumed to maintain the standing wave. Accordingly, a user may periodically provide himself or herself with feedback regarding a rate of fat removal. The amplitude and power monitoring may be implemented by visually monitoring a pair of metering displays.

A device for removing adipose tissue comprises, in accordance with one embodiment of the present invention, an insertion instrument consisting essentially of an elongate rigid tube having a distal end, a proximal end, an external surface and an axially extending lumen with a distal mouth opening located in a transverse plane at the distal end. An ultrasonic waveform generator is operatively connected to the insertion tube for generating an ultrasonic pressure wave and transmitting the ultrasonic wave through the tube to establish a standing wave therein. A suction source is operatively connected to the insertion tube at the proximal end for aspirating fluidic material through the lumen of the tube. A liquid supply is operatively connected to the insertion tube for delivering a liquid to the external surface of the tube at the proximal end thereof, whereupon the liquid is guided along the external surface, in a film adhering to the external surface, toward the distal end of the tube.

This particular embodiment of the invention enables the insertion of a liposuction instrument having a smaller diameter than conventional liposuction devices, thereby restricting the diameters of channels formed in fatty tissues during a lipectomy procedure. A surrounding irrigation jacket as proposed by others would necessitate widening the initial skin incision, and would also enlarge or gouge the individual surgeon-made fat tunnels in an unpredictable way as the cannula is moved in and out.

According to a further feature of the present invention, the device further comprises a temperature control for maintaining the distal end of the insertion tube and adipose tissues at a surgical site located distally of the distal end at approximately body temperature during a generation of the standing wave and the consequent removal of adipose tissues in a lipectomy procedure. Where the ultrasonic pressure wave has a characteristic frequency, the temperature control includes frequency tracking componentry operatively connected to the insertion tube of probe for monitoring changes in a resonant frequency thereof, the frequency tracking componentry being operatively connected to the ultrasonic waveform generator for modifying the characteristic frequency to correspond to the resonant frequency. Of course, the frequency tracking componentry primarily serves to reduce energy losses due to frequency mismatch.

As mentioned hereinabove, the insertion tube may be provided with an elongate groove extending longitudinally along the external surface of the tube for facilitating the guidance of the liquid from the proximal end of the tube towards the distal end.

In accordance with another feature of the present invention, the liposuction device further comprises a first detector operatively connected to the insertion tube or probe for determining, through a sensing of impedance change, an amplitude of reciprocating motion of the distal end of the tube during generation of the ultrasonic wave and a first display operatively connected to the first detector for displaying the measured amplitude in a readable form. In addition, a second detector is operatively connected to the ultrasonic waveform generator for measuring power output thereof during use of the tube to liquefy fattty tissues, while a second display is operatively connected to the second detector for displaying the measured power output in a readable form.

According to yet another feature of the present invention, the tube has a radius and a wall thickness at the distal end, the wall thickness being at least one-third the radius. This proportion enables the provision of a relatively blunt edge at the distal end of the tube, the blunt edge surrounding the mouth opening.

A device for removing adipose tissue comprises, in accordance with a particular embodiment of the present invention, an elongate rigid tube having a distal end, a proximal end, a smooth continuous external surface and an axially extending lumen with a distal mouth opening located in a transverse plane at the distal end. The tube is made of a titanium alloy or aluminum and has a blunt edge at the distal end, the edge surrounding the mouth opening. An ultrasonic waveform generator is operatively connected to the tube for generating an ultrasonic pressure wave having a characteristic frequency between approximately 20 kHz and 24 KHz and transmitting the ultrasonic wave through the tube to establish a standing wave therein. A suction source is operatively connected to the tube at the proximal end for aspirating fluidic material through the lumen. A frequency tracking circuit is operatively connected to the tube for monitoring changes in a resonant frequency thereof, the frequency tracking circuit being operatively connected to the ultrasonic waveform generator for modifying the characteristic frequency to correspond to the resonant frequency. The smooth continuous external surface of the tube, the frequency tracking circuit, the operation of the ultrasonic waveform generator at a relatively low frequency between approximately 20 and 24 KHz, and the material of the tube all serve in part to maintain the distal end and adipose tissues at a surgical site located distally of the distal end at approximately body temperature during a generation of the standing wave and removal of adipose tissues in a lipectomy procedure.

The present invention improves the relatively traumatic and inconsistent liposuction procedure by exposing adipose or fat cells to a phenomenon known as cavitation, before aspirating. Cavitation is a furious bubble activity produced in front of the distal tip of the probe. Cavitation liquefies the fat, which is then easily aspirated. The amount of potentially harmful suction force is much reduced since the fat tissue no longer has to be torn away from its surrounding substrate. Most of the damage to blood vessels is avoided with the present invention because there is no cutting or great suction forces. There is also no excessive heat generated which may damage tissues other than fat. Vessel walls are high in collagen, a material not easily effected by ultrasound or cavitation. Nerve sheaths are made of similar connective tissue. Furthermore, by activating blood platelets, cavitation seals the more delicate capillaries so that bleeding from these small vessels is minimized or prevented. Chemical trauma and inflammation will in this way be greatly reduced and hopefully obviated entirely.

It is well known that cavitation will homogenize body tissue as well as many other materials. This action is variously called disrupting, fragmenting, disintegrating, dispersing, emulsifying, disaggregating, mixing, and breaking up. However, the action of cavitation on fat in accordance with the present invention is different. Cavitation generated at frequencies and with amplitudes in accordance with the present invention causes fat to liquefy, not particlize. There are almost no "pieces" of material produced in the sonicated product as in the usual ultrasonic dispersing process. For example, even the process of emulsification is the breakup of oil or fat into particles (globules), though small enough to more or less stabilize in water or other liquid. While adipose tissue can certainly be emulsified in water, it is not necessary in a method in accordance with the present invention, and there is no need to supply irrigating liquid for emulsifying or for cooling purposes. (Liquid for other purposes may be delivered to the surgical site.) This is quite different from all other ultrasonic probes that remove tissue.

When fat cavitates, the molecules lose their arrangement, or are loosened in some manner, so that the solid becomes liquid. This same liquefying phenomenon occurs in gels, in blood clots, and in the common plastic, methylmethacrylate (LUCITE), which is normally solid. Other body tissues do not behave in this unexpected way.

An ultrasonic cannula in accordance with the present invention has the suction opening at the distal end, rather than at the side. A side hole is standard with all present mechanical instruments, and in the liposuction apparatus disclosed by U.S. Pat. No. 4,886,491 to Parisi. Both fat disruption and fat removal occur directly in front of the cannula tip in accordance with the present invention. The surgeon knows where and how much is being removed. This allows the probe to be accurately positioned and tissue removal to be spot specific. Because the fat is almost instantly liquefied, and to a depth close to the tip-face, the surgeon has accurate control over the amount of fat being removed by his own hand pressure. And with his other hand, the surgeon can feel or pinch the fat immediately in front of the tip where all the action takes place. Feeling for the fat below the skin surface is commonly done in liposuction procedures. The removal pocess can now be more accurate and consistent. Also, when a surgeon inserts an ultrasonic probe in accordance with the present invention into fat, the tissue is not traumatized by cutting, stretching, separation, compression or heating. In the present invention, a fat removal tunnel or channel is made by cavitation and liquefaction only, before the ultrasonic cannula is moved forward.

The probe amplitude and cavitation intensity developed in accordance with the present invention are in a range where other body tissue, such as muscle and connective tissue, as well as nerves and blood vessels, are not easily injured. These other tissues are not liquefied by ultrasound, but must be fragmented or disintegrated to be destroyed, requiring a more intense cavitation.

A cavitation or probe tip in accordance with the present invention has a small diameter hole with a relatively large vibrating surface area. This is different from other tissue removal probes such as those described in U.S. Pat. No. 3,529,129 to Balamuth, U.S. Pat. No. 4,515,583 to Sorich, and U.S. Pat. No. 4,223,676 to Wuchinich, where the tip has a thin edge. A tip configuration in accordance with the present invention minimizes the possibility of removing a plug of fat rather than liquefying removed material. It would be difficult, moreover, not to have a high pressure on a knife-like edge even when handling the ultrasonic probe in a normal way. High pressure combined with a fine edge increases the tendency to fashion a plug, rather than totally process the captured material.

An ultrasonic method of fat removal in accordance with the present invention avoids bloodloss, trauma, and the variable removal rates previously encountered in liposuction operations. Moreover, because of the smooth easy action by this approach on adipose tissue, the surgical operation might now be called body sculpting or contouring. This new method involves a combination of ultrasonic probe techniques which together permit a better and easier operative procedure. Ultrasonic energy is applied directly on the fat to be extracted, under cool conditions, liquefying or, if saline or anesthetic is added, emulsifying the unwanted tissue. The fat liquid is removed at the probe tip and at the moment of liquefaction by the making and breaking of microscopic bubbles. These bubbles collapse or implode with great force, on the order of 150,000 PSI, although on a micron level, and generally act on any soft material to disintegrate, disperse, and emulsify. The sound pressure from the probe is felt, or is effective, only a few millimeters into the adipose tissue in front of the probe tip. The sound wave is not beamed or dispersed into the body like ultrasonic diagnostic or therapy devices.

An ultrasonic method in accordance with the present invention has several important advantages over the standard medical practice of fat removal or liposuction. The ultrasonic probe does not injure nerves. It considerably reduces bleeding. It produces a smoother more even surface than punching holes. The same generator knob setting and speed of movement will produce the same rate of fat removal. The device eases the labor of moving the probe by the surgeon since cavitation is doing all the work; hand pressure, twisting, speed of movement, and scraping are not necessaty, or even useful. Because only a "single pass" is necessary, the new method shortens surgical time which can take several hours. There is no tearing, stretching, or heating of the tissue, and no removing chunks of tissue either due to cutting or high suction pressure. The liquid material aspirated by the pump flows easily since there are few particles or pieces of fat, and further, movement through the suction tube is aided by the ultrasonic vibrations in the tube wall. Seroma or blood clots, if they form, are easily liquefied by cavitation similar to the action on adipose cells, and removed. Since any "treated" material becomes liquid close to the suction point, tissue liquefied or destroyed is not likely to get trapped or remain in the operative area. The objective of the foregoing is to provide a device which can obviate the trauma of present liposuction techniques that include hematoma, seroma, infection, discoloration contour irregularities and cellulite formation.

DETAILED DESCRIPTION

Figure 1:
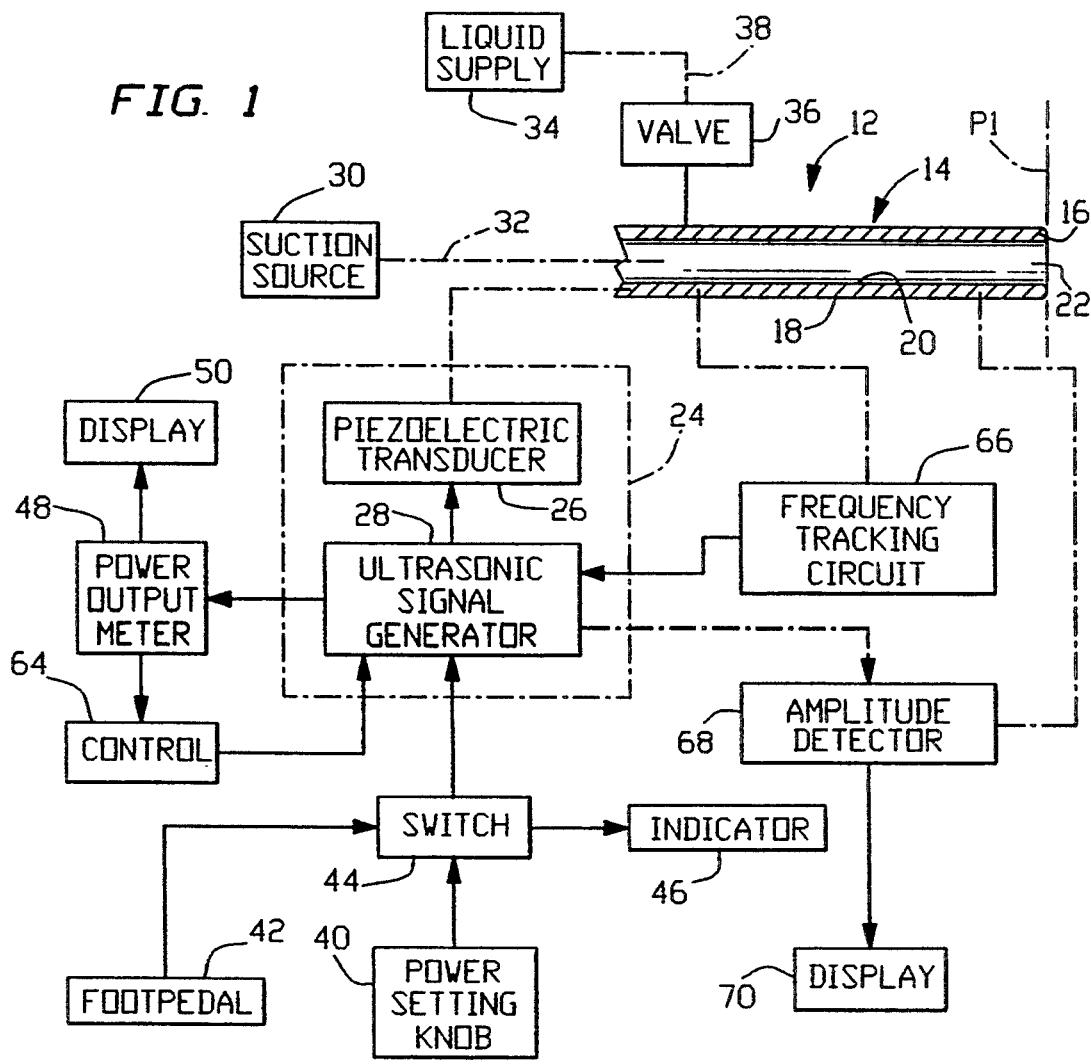
FIG. 1 is basically a block diagram of a liposuction device in accordance with the present invention.

As illustrated in FIG. 1, an ultrasonic liposuction device or system comprises an insertion instrument 12 consisting essentially of an elongate rigid tube or cannula 14 having a distal end 16, a proximal end, an external surface 18 and an axially extending lumen 20. At a distal end, lumen 20 has a mouth opening 22 located in a transverse plane P1. Cannula 14 is made of titanium alloy or aluminum.

An ultrasonic waveform generator 24 is operatively connected to cannula 14 for supplying thereto electrical power in the form of an ultrasonic pressure wave. Generator 24 includes an electromechanical transducer 26 in the form of a piezoelectric crystal and a signal generator 28 operatively connected to the transducer from feeding an ultrasonic alternating or pulsed electrical signal thereto. Transducer 26 converts electrical energy into mechanical vibrations which are transmitted through cannula 14 to establish a longitudinal standing wave therein.

During use of the device of FIG. 1, adipose tissue is liquefied in front of distal end 16 and aspirated through lumen 20 in response to a force applied to lumen 20 by a suction source 30. Suction source 30 is connected to lumen 20 via a noncollapsible hose 32 which is attached to a bottle (not shown) acting as a collector or suction trap. The vacuum is less than atmospheric, about 28" Hg and can be provided by a standard suction pump or a built-in hospital supply.

A liquid supply or pump 34 is provided for supplying any desired liquid to a surgcial site during a liposuction procedure using tube or probe 14. Such liquids include saline, antiseptic, anesthetic, hyaluronidase, heparin and epinephrine. Cool saline may be used for its anesthetic effect or to facilitate so-caleed skin pinching in front of cannula 14.

Under the control of a shut-off valve 36, liquid from supply 34 travels through a liquid line 38 to the proximal end of cannula 14 where the liquid is deposited on external tube surface 18. The liquid adheres to surface 18 and runs in a layer or film along cannula 14 towards distal end 16. Since cannula 14 is almost pitched downwardly into the patient, the liquid will tend to flow down the cannula 14 in a thin film.

As additionally illustrated in FIG. 1, generator 24 is provided with a power setting control knob 40. Alternatively, the power output may be varied by a footpedal 42. Footpedal 42 and knob 40 are connected to generator 24 via a switch 44 which provides the surgeon the option of choosing one control or the other. An indicator light 46 is connected to switch 44 for indicating whether knob 40 or footpedal 42 is connected to generator 24.

A watt meter 48 is connected to generator 24 for detecting or measuring the power output of the generator. Meter 48 is linked to a display 50 which provides a visual indication of the power. Mechanical and electrical fault indicator lights (not shown) may also be provided.

Figure 2:
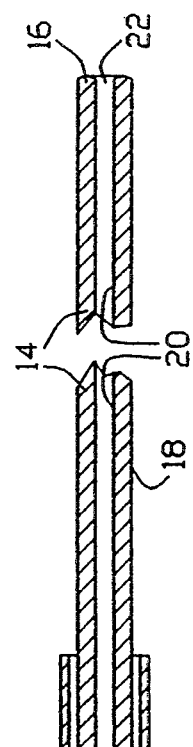
FIG. 2 is partially a block diagram and partially a schematic longitudinal cross-sectional view of an insertion tube or probe included in the liposuction device or system of FIG. 1.

Generator 24 preferably operates at 22.5 KHz and supplies up to 70 watts of power to transducer 26. As illustrated in FIG. 2, transducer 26 includes a plurality of piezoelectric crystals 52 which are embedded in a handpiece 54. Handpiece 54 is, for example, 6 inches long and 1.25 inches in diameter and weighs 6 ounces. Handpiece 54 serves in part to amplify the ultrasonic waves generated by piezoelectric crystals 52. To that end, handpiece 54 includes a stepped or tapered horn portion 56 which acts a velocity transformer that increases amplification.

As shown in FIGS. 1 and 2, distal end 16 is formed with a blunt circular edge surrounding mouth opening 22. The blunt edge prevents damage to blood vessels as cannula 14 is moved through a surgical site. The open-end design of cannula 14 allows for immediate removal of liquefied fat. The fat is liquefied by cavitation produced by the ultrasonically vibrating distal end 16 of cannula 14 and is aspirated through lumen 20 owing to the suction force provided by source 30.

As further illustrated in FIG. 2, liquid from supply 34 is fed via one or more conduits 58 and 60 in handpiece 54 to the proximal end of cannula 14. The liquid then flows in a thin film down external surface 18 of cannula 14 under the action of gravity. Alternatively, under the control of valve 36, a liquid bolus may be passed through lumen 20 to the surgical site. The bolus moves to lumen 20 through an auxiliary channel 62 provided in handpiece 54 parallel to lumen 20 and is fed to channel 62 and lumen 20 during a temporary deactivation or shut-off of suction source 30.

The rate at which cannula 14 liquefies fat is a function of amplitude. Normally, when cannula 14 presses on tissue or meets tissue having more resistance, the tip movement tends to be slowed, which reduces efficiency. To compensate for this phenomenon, generator 24 is provided with a circuit 64 (FIG. 1) which senses impedance change and automatically increases the power to cannula 14 to maintain amplitude.

Similarly, temperature and varied conditions and viscosities in the human body change the natural resonant frequency of the cannula 14 and cause wide swings in efficiency, of which the surgeon may not be aware. To compensate for this eventuality, a frequency tracking circuit 66 (FIG. 1) is operatively connected to cannula 14 and generator 24 autoamtically adjusting the operating frequency of generator 24 to accord with the changed resonant frequency of cannula 14. Tracking circuit 66 serves in part to control temperature of cannula 14 and, conomitantly, adipose tissues at a surgical site located distally of distal end 16, so that fat liqeuaction takes place at approximately body temperature.

FIG. 1 also shows an amplitude meter or detector 68 operatively coupled to cannula 14 and/or generator 24 for detecting or measuring the excursion of distal end 16 during a sonication procedure. The excursion or amplitude of the distal end 16 of cannula 14 is communicated to a user via a display 70.

Watt meter 48 and amplitude detector 68, with their associated displays 50 and 70, enable a user to immediately gauge the rate of fat removal. For example, if the amplitude remains the same while the power increases, the user knows that he is pressing harder and the removal rate will increase.

Cannula 14 operates at an amplitude of approximately 3 mils (0.075"). At this amplitude, fat is easily liquefied or emulsified without damage to surrounding tissue. No external cooling is necessary owing to several design factors, namely, frequency tracking circuit 66, the operation at a relatively low frequency, within a few kilohertz of 22 KHz, the use of a cannula 14 with a smooth external surface 18, and the composition of cannula 14 as titanium alloy or aluminum. Low operating frequency reduces the number of nodes and antinodes along cannula 14. There is also less loss in a transmission line. Air cooling, body fluids or suction flow cooperate to maintain the horn and cannula 14 just above body temperature. All liquid and electrical lines are connected to handpiece 54 at the base thereof so that there is no interference with operation.

Figure 4:
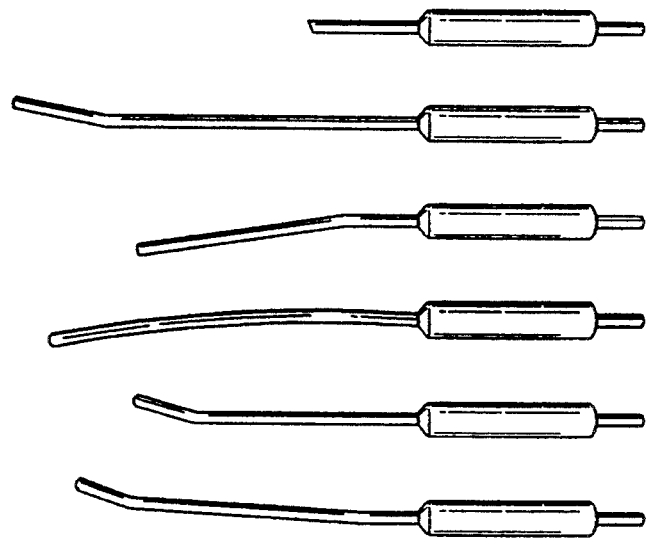
FIG. 4 illustrates different shapes for liposuction probes.
Figure 4:
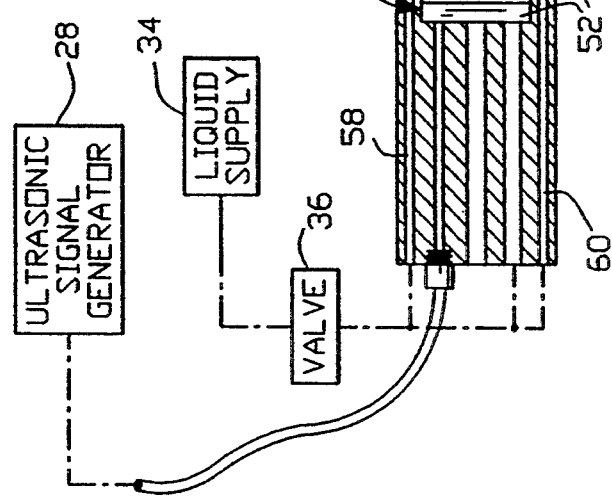

Cannula 14 is approximately one foot in length and is removably attached to handpiece 54 for enabling replacement at the operating table with probes of different lengths and shapes (see FIG. 4).

In use of the system of FIGS. 1 and 2, a patient's skin surface is marked with contour lines indicating where fat is to be removed. An incision, for example, 2 cm long, is formed in the patient's skin. Cannula 14 is inserted through the incision and positioned in an subcutaneous adipose tissue plane. Upon the locating of the lipolysis site, ultrasonic signal generator 24 is activated by knob 40 or footpedal 42. Adipose tissue located ahead of distal end 16 is liquefied by cavitation and simultaneously removed through the action of suction source 30. Footpedal 42 is advantageous in freeing the surgeon's hands and enabling him to vary the amount of power supplied. When the footpedal is not depressed, no power is transmitted to cannula 14.

During sonication, the position and progression of the distal end 16 of cannula 14 are easily monitored by the surgeon since the fat tissue loses resistance as it is liquefied. Cavitation liquefies the fat at approximately body temperature, while leaving blood vessels and nerve sheaths intact. Because fat removal is localized and because liquefying the fat provides surgical feel, the surgeon is able to sculpt the tissues more accurately than in conventional methods. Thus, a more uniform result is achievable.

Upon the removal of fat from all designated areas and the removal of cannula 14 from the patient, a standard drain is inserted through the incision and secured with 2-0 silk. The incision is closed using standard surgical procedure.

Figure 3:
FIG. 3 is a partial schematic side elevational view of a modified insertion tube or probe for use in a method in accordance with the present invention.

As illustrated in FIG. 3, cannula 14 may be optionally provided along external surface 18 with a plurality of longitudinally extending grooves or striations 72. Grooves 72 serve to enhance the conveyance of liquid from liquid supply 34 to a surgical site at distal end 16. Grooves 72 facilitate fluid conduction especially at the skin surface and in the underlying tissues. Grooves 72 are approximately ¼ mm wide and ¼ mm deep, with about 10 grooves on cannula 14.

The feeding of liquid in a thin film along external surface 18 and/or through grooves 72 enables liposuction cannula 14 to have a smaller diameter than conventional liposuction devices. This restriction in diameter is advantageous because it results in the formation of narrower channels or tunnels in fatty tissues during a lipectomy procedure.

Rat studies are used as an established model for liposuction. Preliminary tests on these animals have shown that the time required for effective sonication of almost all parauterine fat is less than 10 seconds, while removal of the same fat using liposuction alone, without sonication, takes 2-25 seconds and causes considerable bleeding. Fat removal in cadavers is also significantly faster with sonication. The rate is about ½ cc of fat per second. Studies on nerves show that there is no injury or decrease in nerve condition if the tip amplitude of the present invention is kept to less than 3½ mils (about 0.090"). Other ultrasonic probe devices typically injure the nerves. See "A Morphological Study of the Effect of Cavitron Ultrasonic Surgical Aspirator Near Peripheral Nerves," Michael Gleeson, Arch Otol, Head Neck Surgery, Vol 113, May 1987, and "The Use Of High Frequency Ultrasound For Dissection of Small Diameter Blood Vessels and Nerves," Paul Fisher, Krishna Narayanan, Am Plastic Surgery, 1992, 28:326-330.

An in vivo study on pig fat using liposuction in accordance with the present invention showed that the fat tissue was removed easily without the necessity of repeated thrusts in the same tunnel. There was no need for cooling water, and very little bleeding was produced. When saline irrigation was incorporated as well, an examination of the suction bottle reservoir showed that there was a liquid layer of fat on top of the water and almost no particles or pieces of tissue. Only a small amount of blood was evident in the bottle.

Cannula 14 preferably has a substantial wall thickness, especially at distal end 16. Preferably, the wall has a thickness of approximately one-third the radius of the probe. This wall thickness, as well as the rounded edge of distal end 16, serves to prevent the formation of tissue chunks. Such chunks can become stuck inside the cannula and result in a reduction in the control of the surgeon over the extent and rate of tissue removal.

A liposuction instrument and associated method in accordance with the present invention serve to obviate the trauma of prior art techniques, which includes hematoma, seroma, infection, discoloration, contour irregularities, and cellulite formation. The method also yields more consistent results that prior art methods.

An instrument in accordance with the present invention can be assembled quickly and easily prior to surgery and can be easily sterilized.

The open distal end 16 of cannula 14 allows the probe to be accurately positioned and the tissue removal spot specific. Fat removal occurs only in front of the distal end 16 of cannula 14 and not to the side so that the cannula 14 does not have to be twisted or turned. The surgeon has greater control over the amount of fat being removed.

It is to be noted that an ultrasonic liposuction probe in accordance with the present invention operates most effectively with an amplitude of 2 to 4 mils. If the amplitude falls below 2 mils, cavitation will be insufficient to liquefy fatty tissue, whereas if the amplitude rises above 4 mils, nonfatty tissue such as nerves and blood vessels will be injured.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A liposuction method comprising the steps of:
providing an elongate rigid tube having a distal end and a proximal end and an axially extending lumen;
forming an incision in a skin surface of a patient;
inserting only said tube through said incision into subcutaneous adipose tissues of the patient;
upon insertion of said tube through said incision, generating an ultrasonic pressure wave at said proximal end of said tube;
transmitting said ultrasonic wave through said tube to establish a longitudinal standing wave therein;
producing cavitation bubbles at said distal end of said tube in response to said standing wave;
by virtue of the production of said cavitation bubbles, liquefying adipose tissues of the patient at a surgical site located distally of said distal end;
applying suction to said lumen, thereby aspirating the liquefied adipose tissues from said surgical site through said lumen; and
maintaining said distal end and said adipose tissues at said surgical site at approximately body temperature during said steps of producing cavitation bubbles and liquefying.

2. The method defined in claim 1 wherein said tube has an external surface, further comprising the step of delivering a surgical liquid to said surgical site during said steps of producing cavitation bubbles and liquefying, said step of delivering including the step of guiding said liquid in a film along said external surface towards said distal end.

3. The method defined in claim 2 wherein said step of guiding includes the step of maintaining said liquid in said film solely by adhesion of the liquid to said external surface.

4. The method defined in claim 2 wherein said tube is provided along said external surface with at least one longitudinally extending groove, said step of guiding including the step of transferring said liquid along said groove toward said distal end.

5. The method defined in claim 1 wherein said distal end undergoes a reciprocating motion due to said standing wave, further comprising the steps of monitoring amplitude of said reciprocating motion and monitoring power consumed to maintain said standing wave during said steps of generating, transmitting, producing and liquefying, thereby determining a rate of fat removal.

6. The method defined in claim 5 wherein said steps of monitoring include the step of visually monitoring a pair of metering displays.

7. The method defined in claim 1 wherein said tube has an external surface, further comprising the step of delivering a surgical liquid to said surgical site, said step of delivering including the steps of guiding said liquid in a film along said external surface towards said distal end and maintaining said liquid in said film solely by adhesion of the liquid to said external surface.

8. The method defined in claim 1 wherein said step of producing cavitation bubbles includes the step of longitudinally vibrating said distal end with an amplitude between 2 mils and 4 mils.

9. A liposuction device comprising:
an insertion instrument consisting essentially of an elongate rigid tube having a distal end, a proximal end, an external surface and an axially extending lumen with a distal mouth opening at said distal end;
generating means operatively connected to said tube for generating an ultrasonic pressure wave and transmitting said ultrasonic wave through said tube to establish a longitudinal standing wave therein, said ultrasonic pressure wave having a characteristic frequency;
suction means operatively connected to said tube at said proximal end for aspirating fluidic material through said lumen; and
frequency tracking means operatively connected to said tube for monitoring changes in a resonant frequency thereof, said frequency tracking means being operatively connected to said generating means for modifying said characteristic frequency to correspond to said resonant frequency.

10. The device defined in claim 9 wherein said tube is provided with an elongate groove extending longitudinally along said external surface, said groove serving to guide said liquid from said proximal end towards said distal end.

11. The device defined in claim 9, further comprising:
first measuring means operatively connected to said tube for determining an amplitude of reciprocating motion of said distal end of said tube during generation of said ultrasonic wave;
first display means operatively connected to said first measuring means for displaying the measured amplitude in a readable form;
second measuring means operatively connected to said generating means for measuring power output thereof during use of said tube to liquefy fatty tissues;
second display means operatively connected to said second measuring means for displaying the measured power output in a readable form.

12. The device defined in claim 9 wherein said tube is made of titanium.

13. The device defined in claim 9 wherein said tube is made of aluminum.

14. The device defined in claim 9 wherein said tube has a radius and a wall thickness at said distal end, said wall thickness being at least one-third said radius.

15. The device defined in claim 9 wherein said tube has a blunt edge at said distal end, said blunt edge surrounding said mouth opening.

16. A liposuction device comprising:
an elongate rigid tube having a distal end, a proximal end, an external surface and an axially extending lumen with a distal mouth opening;
generating means operatively connected to said tube for generating an ultrasonic pressure wave and transmitting said ultrasonic wave through said tube to establish a longitudinal standing wave therein;
suction means operatively connected to said tube at said proximal end for aspirating fluidic material through said lumen;
first measuring means operatively connected to said tube for determining an amplitude of reciprocating motion of said distal end of said tube during generation of said ultrasonic wave;
first display means operatively connected to said first measuring means for displaying any of a multiplicity of possible measured amplitudes in a readable form;
second measuring means operatively connected to said generating means for measuring power output thereof during use of said tube to liquefy fatty tissues; and
second display means operatively connected to said second measuring means for displaying any of a multiplicity of possible measured power outputs in a readable form.

17. The device defined in claim 16, further comprising temperature control means for maintaining said distal end and adipose tissues at a surgical site located distally of said distal end at approximately body temperature during a generation of said standing wave and removal of adipose tissues in a lipectomy procedure.

18. The device defined in claim 17 wherein said ultrasonic pressure wave has a characteristic frequency, said temperature control means including frequency tracking means operatively connected to said tube for monitoring changes in a resonant frequency thereof, said frequency tracking means being operatively connected to said generating means for modifying said characteristic frequency to correspond to said resonant frequency.

19. The device defined in claim 16 wherein said tube is provided with an elongate groove extending longitudinally along said external surface, said groove serving to guide said liquid from said proximal end towards said distal end.

20. The device defined in claim 16 wherein said tube is made of titanium.

21. The device defined in claim 16 wherein said tube is made of aluminum.

22. The device defined in claim 16 wherein said tube has a radius and a wall thickness at said distal end, said wall thickness being at least one-third said radius.

23. The device defined in claim 16 wherein said tube has a blunt edge at said distal end, said blunt edge surrounding said mouth opening.

24. A liposuction device for removing adipose tissue, comprising:
an elongate rigid tube having a distal end, a proximal end, a smooth continuous external surface and an axially extending lumen with a distal mouth opening located in a transverse plane at said distal end, said tube being made of a substance selected from the group of titanium alloy and aluminum, said tube having a blunt edge at said distal end, said edge surrounding said mouth opening;
generating means operatively connected to said tube for generating an ultrasonic pressure wave having a characteristic frequency between approximately 18 kHz and 26 KHz and transmitting said ultrasonic wave through said tube to establish a standing wave therein;
suction means operatively connected to said tube at said proximal end for aspirating fluidic material through said lumen; and
frequency tracking means operatively connected to said tube for monitoring changes in a resonant frequency thereof, said frequency tracking means being operatively connected to said generating means for modifying said characteristic frequency to correspond to said resonant frequency,
said smooth continuous external surface of said tube, said frequency tracking means, the operation of said generating means at a relatively low frequency between approximately 18 and 26 KHz, and the material of said tube all serving in part to maintain said distal end and adipose tissues at a surgical site located distally of said distal end at approximately body temperature during a generation of said standing wave and removal of adipose tissues in a lipectomy procedure.

25. The probe defined in claim 16 wherein said tube is provided with an elongate groove extending along said external surface from essentially said proximal end to said distal end, said groove serving to guide liquid from said proximal end towards said distal end.

26. A liposuction method comprising the steps of:
providing an elongate rigid tube having a distal end and a proximal end and an axially extending lumen;
forming an incision in a skin surface of a patient;
inserting said tube through said incision into subcutaneous adipose tissues of the patient;
upon insertion of said tube through said incision, generating an ultrasonic pressure wave at said proximal end of said tube;
transmitting said ultrasonic wave through said tube to establish a longitudinal standing wave therein, said distal end undergoing a reciprocating motion due to said standing wave;
liquefying adipose tissues of the patient at a surgical site located distally of said distal end;
applying suction to said lumen, thereby aspirating the liquefied adipose tissues from said surgical site through said lumen; and
monitoring amplitude of said reciprocating motion and power consumed to maintain said standing wave during said steps of transmitting and liquefying to thereby determine a rate of fat removal.

27. The method defined in claim 26, further comprising the steps of:
measuring amplitude of said reciprocating motion;
displaying the measured amplitude on a first meter;
measuring power consumed to maintain said standing wave;
displaying the measured power on a second meter.

28. The method defined in claim 27 wherein said step of monitoring includes the step of visually monitoring said first meter and said second meter.

29. A liposuction method comprising the steps of:

providing an elongate rigid tube having a distal end and a proximal end and an axially extending lumen;

forming an incision in a skin surface of a patient;

inserting said tube through said incision into subcutaneous adipose tissues of the patient;

upon insertion of said tube through said incision, generating an ultrasonic pressure wave at said proximal end of said tube;

transmitting said ultrasonic wave through said tube to establish a longitudinal standing wave therein;

liquefying adipose tissues of the patient at a surgical site located distally of said distal end;

applying suction to said lumen, thereby aspirating the liquefied adipose tissues from said surgical site through said lumen;

automatically measuring a resonant frequency of said tube during said steps of transmitting and liquefying; and in response to detecting changes in said resonant frequency during said step of measuring, automatically modifying a characteristic frequency of said ultrasonic pressure wave to correspond to said resonant frequency.

* * * * *